US012618005B2

(12) United States Patent
Yu et al.

(10) Patent No.: US 12,618,005 B2
(45) Date of Patent: May 5, 2026

(54) LIGHT EMITTING ELEMENT AND MANUFACTURING METHOD THEREOF

(71) Applicant: Samsung Display Co., LTD., Yongin-si (KR)

(72) Inventors: Sang Hee Yu, Hwaseong-si (KR); Hoi-Lim Kim, Seoul (KR); Jae Hong Park, Seoul (KR); Gyu Bong Kim, Suwon-si (KR); Seung Uk Noh, Seoul (KR); Ju Yon Lee, Cheonan-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 1001 days.

(21) Appl. No.: 17/836,214

(22) Filed: Jun. 9, 2022

(65) Prior Publication Data

US 2023/0002313 A1 Jan. 5, 2023

(30) Foreign Application Priority Data

Jun. 10, 2021 (KR) ........................ 10-2021-0075389

(51) Int. Cl.
*C07C 309/73* (2006.01)
*B82Y 30/00* (2011.01)
(Continued)

(52) U.S. Cl.
CPC ........... *C09K 11/0811* (2013.01); *B82Y 30/00* (2013.01); *C07C 309/65* (2013.01); *C07C 309/73* (2013.01); *C09K 11/0816* (2013.01); *C09K 11/582* (2013.01); *C09K 11/62* (2013.01); *C09K 11/64* (2013.01); *C09K 11/661* (2013.01); *H10K 71/40* (2023.02); *B82Y 20/00* (2013.01);
(Continued)

(58) Field of Classification Search
None
See application file for complete search history.

(56) References Cited

U.S. PATENT DOCUMENTS 6,627,384 B1 * 9/2003 Kim .......................... G03F 7/40 430/326
10,227,450 B2 3/2019 Jung et al.
(Continued)

FOREIGN PATENT DOCUMENTS

JP 2001-188341 * 7/2001
JP 2009510795 * 3/2009
(Continued)

OTHER PUBLICATIONS

Korean Office Action dated Dec. 18, 2024, in Korean Patent Application No. 10-2021-0075389.
(Continued)

*Primary Examiner* — Tae H Yoon
(74) *Attorney, Agent, or Firm* — CANTOR COLBURN LLP

(57) ABSTRACT

A light emitting element according to an embodiment includes a first electrode, a second electrode overlapping the first electrode, an emission layer disposed between the first electrode and the second electrode, and an electron transport region disposed between the emission layer and the second electrode, wherein the electron transport region includes a thermal acid generator (TAG). A method of manufacturing a light emitting element is also provided.

16 Claims, 11 Drawing Sheets

(51) Int. Cl.

| | |
|---|---|
| ***C07C 309/65*** | (2006.01) |
| ***C09K 11/08*** | (2006.01) |
| ***C09K 11/58*** | (2006.01) |
| ***C09K 11/62*** | (2006.01) |
| ***C09K 11/64*** | (2006.01) |
| ***C09K 11/66*** | (2006.01) |
| ***H10K 71/40*** | (2023.01) |
| *B82Y 20/00* | (2011.01) |
| *H10K 50/115* | (2023.01) |
| *H10K 50/16* | (2023.01) |
| *H10K 50/17* | (2023.01) |

(52) U.S. Cl.

CPC ............ *H10K 50/115* (2023.02); *H10K 50/16* (2023.02); *H10K 50/171* (2023.02)

(56) References Cited

U.S. PATENT DOCUMENTS

| | | | | |
|---|---|---|---|---|
| 10,818,860 | B2 | 10/2020 | Sokolov et al. | |
| 11,367,835 | B2 | 6/2022 | Sokolov et al. | |
| 2009/0039764 | A1* | 2/2009 | Cho ....................... | B82Y 30/00 313/504 |
| 2019/0252618 | A1 | 8/2019 | Grigg et al. | |
| 2020/0066993 | A1 | 2/2020 | Li et al. | |
| 2020/0185604 | A1 | 6/2020 | Grigg et al. | |

FOREIGN PATENT DOCUMENTS

| | | |
|---|---|---|
| KR | 10-2004-0046350 | 6/2004 |
| KR | 10-2006-0101184 | 9/2006 |
| KR | 10-2008-0063764 | 7/2008 |
| KR | 10-2012-0095741 | 8/2012 |
| KR | 10-2016-0076133 | 6/2016 |
| KR | 10-2017-0008038 | 1/2017 |
| KR | 10-2019-0020072 | 2/2019 |
| KR | 10-1995371 | 7/2019 |
| KR | 10-2125204 | 6/2020 |

OTHER PUBLICATIONS

Krishna P. Acharya et al., "High Efficiency Quantum Dot Light Emitting Diodes from Positive Aging", Royal Society of Chemistry, Nanoscale, Aug. 25, 2017, pp. 1-8.

Qiang Su et al., "Origin of Positive Aging in Quantum-Dot Light-Emitting Diodes", Advanced Science, 2018, pp. 1-7, No. 1800549.

Sang-Do Lee et al., "Cationic Polymerization Behavior of Isobutyl Vinyl Ether with Arenesulfonates as Non-Salt-Type Latent Thermal Initiators", Journal of Polymer Science: Part A: Polymer Chemistry, 1999, pp. 293-301, vol. 37.

Thermal Acid Generators, Heraeus, https://www.heraeus.com/en/hep/products_hep/ultra_pure_chemicals/thermal_acid_generators_1/thermal_acid_generators_1.html, retrieved Feb. 2, 2021.

* cited by examiner

LIGHT EMITTING ELEMENT AND MANUFACTURING METHOD THEREOF

CROSS-REFERENCE TO RELATED APPLICATION(S)

This application claims priority to and benefits of Korean Patent Application No. 10-2021-0075389 under 35 U.S.C. § 119, filed on Jun. 10, 2021 in the Korean Intellectual Property Office, the entire contents of which are incorporated herein by reference.

BACKGROUND

1. Technical Field

The disclosure relates to a light emitting element and a manufacturing method thereof.

2. Description of the Related Art

A light emitting element is an element in which electrical energy is converted into light energy. Examples of such a light emitting element include an organic light emitting element using an organic material for an emission layer, a quantum dot light emitting element using quantum dots for an emission layer, and the like.

The light emitting element includes a first electrode disposed on a substrate, and a hole transport region, an emission layer, an electron transport region, and a second electrode that are sequentially disposed on the first electrode.

Holes injected from the first electrode move to the emission layer via the hole transport region, and electrons injected from the second electrode move to the emission layer via the electron transport region. Carriers such as holes and electrons recombine in the emission layer to generate excitons. Light is generated as the excitons transition from an exited state to a ground state.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

Embodiments provide a light emitting element with increased luminous efficiency and light emitting life-span through a TAG provided to an electron transport region and a manufacturing method thereof.

According to an embodiment, a light emitting element may include a first electrode, a second electrode overlapping the first electrode, an emission layer disposed between the first electrode and the second electrode, and an electron transport region disposed between the emission layer and the second electrode, wherein the electron transport region may include a thermal acid generator (TAG).

The electron transport region may include a first material in which $H^+$ is separated from the TAG.

The electron transport region may further include inorganic nanoparticles.

The $H^+$ may be bonded to the inorganic nanoparticles.

The TAG may include a sulfonate-based compound.

The TAG may include a compound represented by Chemical Formula 1:

[Chemical Formula 1]

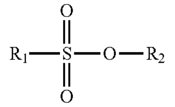

In Chemical Formula 1, $R_1$ and $R_2$ may each independently be a substituted or unsubstituted C3 to C40 alkyl group, a substituted or unsubstituted C3 to C40 aliphatic hydrocarbon group, a substituted or unsubstituted C6 to C40 aromatic hydrocarbon group of C6 to C40, or a combination thereof The compound represented by Chemical Formula 1 may include at least one compound each independently represented by one of Chemical Formula 2-1, Chemical Formula 2-2, Chemical Formula 2-3, Chemical Formula 2-4, Chemical Formula 2-5, Chemical Formula 2-6, Chemical Formula 2-7, Chemical Formula 2-8, Chemical Formula 3-1, Chemical Formula 3-2, Chemical Formula 3-3, Chemical Formula 3-4, Chemical Formula 3-5, and Chemical Formula 3-6:

[Chemical Formula 2-1]

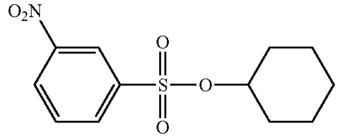

[Chemical Formula 2-2]

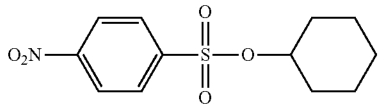

[Chemical Formula 2-3]

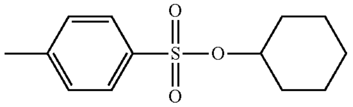

[Chemical Formula 2-4]

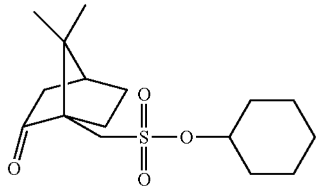

[Chemical Formula 2-5]

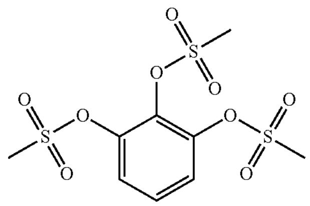

-continued

[Chemical Formula 2-6]

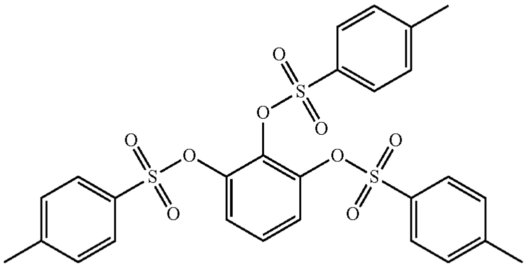

[Chemical Formula 2-7]

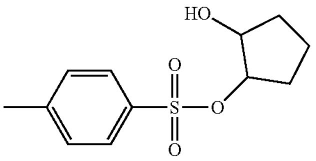

[Chemical Formula 2-8]

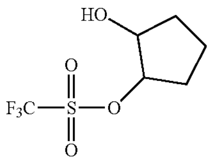

[Chemical Formula 3-1]

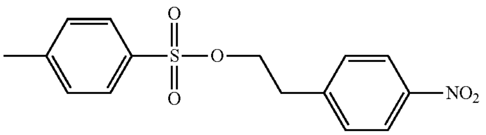

[Chemical Formula 3-2]

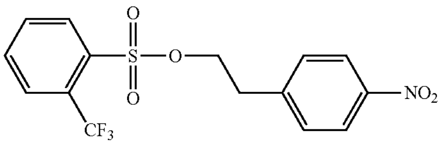

[Chemical Formula 3-3]

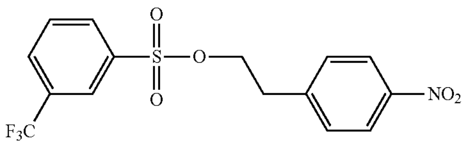

[Chemical Formula 3-4]

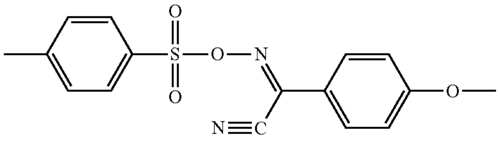

[Chemical Formula 3-5]

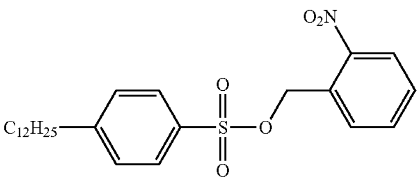

-continued

[Chemical Formula 3-6]

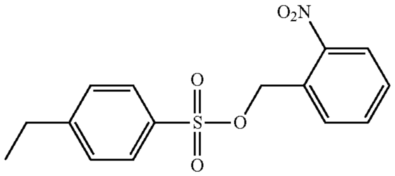

The emission layer may include quantum dot.

The first electrode may be an anode, the second electrode may be a cathode, and the electron transport region may include at least one of a hole blocking layer, an electron transport layer, and an electron injection layer.

According to an embodiment, a method of manufacturing a light emitting element may include forming a first electrode, forming an emission layer on the first electrode, forming an electron transport region on the emission layer, and forming a second electrode on the electron transport region, wherein the forming of the electron transport region may include applying a solution including inorganic nanoparticles and a thermal acid generator (TAG), and curing the solution.

The TAG may include a sulfonate-based compound.

The TAG may include a compound represented by Chemical Formula 1.

The compound represented by Chemical Formula 1 may include at least one compound each independently represented by Chemical Formula 2-1 to Chemical Formula 2-8.

The compound represented by Chemical Formula 1 may include at least one compound each independently represented by Chemical Formula 3-1 to Chemical Formula 3-6.

The emission layer may include quantum dots.

In the curing of the solution, the TAG may generate $H^+$.

The curing may be carried out at a first temperature in a range of about 100 degrees (° C.) to about 150 degrees (° C.).

The method of manufacturing the light emitting element may further include aging after the curing the solution.

The aging may be carried at a second temperature that is lower than the first temperature.

The $H^+$ generated in the curing may be adsorbed to the inorganic nanoparticle or may separate a branch part adsorbed to the inorganic nanoparticle.

According to the embodiments, the light emitting element may have high efficiency and long life-span.

BRIEF DESCRIPTION OF THE DRAWINGS

The above and other aspects and features of the disclosure will become more apparent by describing in detail embodiments thereof with reference to the attached drawings, in which.

DETAILED DESCRIPTION OF THE EMBODIMENTS

Figure 1A:
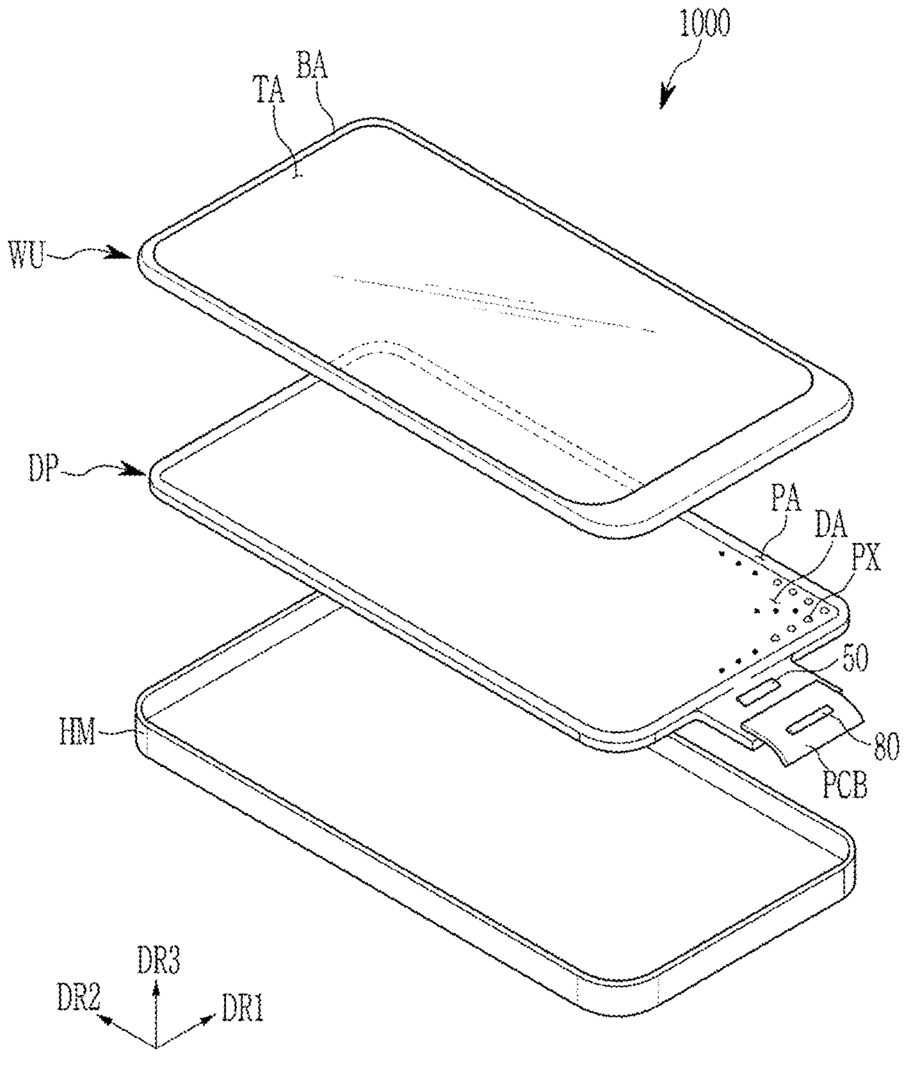
FIG. 1A is an exploded perspective view of a display device according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the description, it will be understood that when an element (or region, layer, part, etc.) is referred to as being "on", "connected to", or "coupled to" another element, it can be directly on, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the description, when an element is "directly on," "directly connected to," or "directly coupled to" another element, there are no intervening elements present. For example, "directly on" may mean that two layers or two elements are disposed without an additional element such as an adhesion element therebetween.

As used herein, the expressions used in the singular such as "a," "an," and "the," are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

In the specification and the claims, the term "at least one of" is intended to include the meaning of "at least one selected from the group of" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The phrase "in a plan view" means viewing the object from the top, and the phrase "in a schematic cross-sectional view" means viewing a cross-section of which the object is vertically cut from the side.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, ±10%, or ±5% of the stated value.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

Figure 1B:
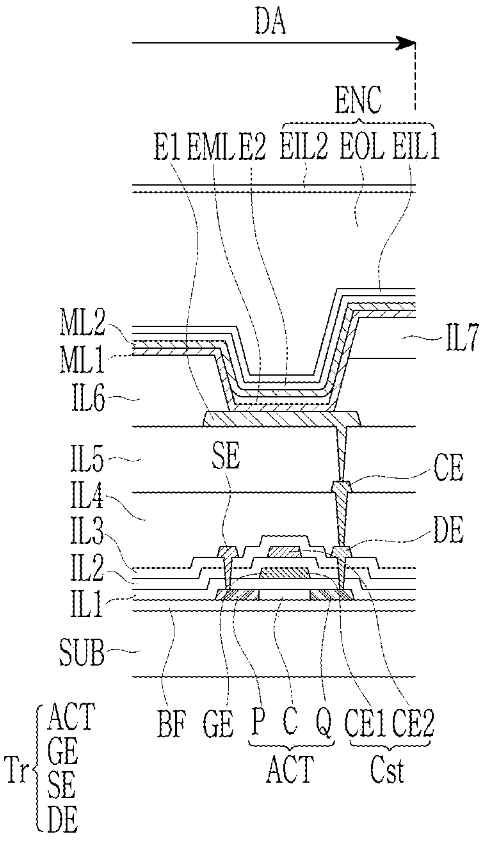
FIG. 1B is a schematic cross-sectional view of a pixel according to an embodiment.

Hereinafter, referring to FIG. 1A and FIG. 1B, a display device according to an embodiment will be described. FIG. 1A is an exploded perspective view of a display device according to an embodiment, and FIG. 1B is a schematic cross-sectional view of a pixel according to an embodiment.

Referring to FIG. 1A, a display device 1000 displays an image toward a third direction DR3 on a plane defined by a first direction DR1 and a second direction DR2. A front (or top) side and a back (or bottom) side of each member are separated by the third direction DR3. Directions indicated by the first to third directions DR1, DR2, and DR3 are relative concepts and may be converted into other directions.

The display device 1000 of FIG. 1A may display a motion picture or a still image. The display device 1000, for example, can be used as a portable electronic device such as a mobile phone, a smart phone, a tablet personal computer, a mobile communication terminal, an electronic notebook, an electronic book, a portable multimedia player (PMP), a navigation device, an ultra mobile PC (UMPC), and the like, as well as a display screen of various products such as a television, a laptop, a monitor, an advertisement board, an Internet of things (IOT), and the like. The display device 1000 according to an embodiment can be used in a wearable device such as a smart watch, a watch phone, a spectacles-type display, and a head mounted display (HMD). The display device 1000 according to an embodiment can be used as a display disposed in an instrument panel (substrate) of a vehicle, a center fascia of the vehicle, or a center information display (CID) disposed on a dashboard, and a room mirror display that replaces a side mirror of the vehicle, and a display disposed on the back of the front seat for entertainment for the rear seat of the vehicle. In FIG. 1A, the display device 1000 according to an embodiment is illustrated as a smart phone for better understanding and ease of description. However, embodiments are not limited thereto.

The display device 1000 according to an embodiment includes a cover window WU, a display panel DP, and a housing member HM. In an embodiment, the cover window WU, the display panel DP, and the housing member HM are combined such that the display device 1000 can be formed.

The cover window WU is disposed on the display panel DP and protects the display panel DP. The cover window WU may include a polyimide window or an ultra-thin glass window.

The cover window WU may include a transmission area TA and a blocking area BA. The transmission area TA is an optically transparent area, and may be an area that transmits incident light. The blocking area BA may be an area having relatively low light transmittance compared to the transmission area TA. The blocking area BA defines the shape of the transmission area TA. The blocking area BA may surround the transmission area TA. The blocking area BA may have a predetermined color. The blocking area BA may overlap the peripheral area PA of the display panel DP to block the peripheral area PA from being viewed from the outside.

The display panel DP may be a flat rigid display panel or a flexible display panel without being limited thereto. The display panel according to an embodiment may be a light emitting display panel, but is not limited thereto. For example, the display panel may be an organic light emitting panel or a quantum dot light emitting display panel. An emission layer of the organic light emitting panel may include an organic light emitting material. An emission layer of the quantum dot light emitting display panel may include quantum dots and quantum rods.

The display panel DP displays an image on the front. The front side of the display panel DP includes a display area DA and a peripheral area PA. The image is displayed in the display area DA. The peripheral area PA may surround the display area DA.

The display panel DP may include pixels PX disposed in the display area DA. Each pixel PX may display light in response to an electrical signal. The light displayed by the pixels PX can implement an image. The number of transistors, the number of capacitors, and the connection relationship included in a pixel PX can be variously modified.

The display panel DP extends from the display area DA and includes signal lines and the peripheral area PA in which the pad portion is disposed. A data driver 50 may be disposed in the peripheral area PA. According to an embodiment, the pad portion of the peripheral area PA may be electrically connected to a printed circuit board PCB that includes a driving chip 80.

The housing member HM is disposed on a lower side of the display panel DP. The housing member HM is combined with the cover window WU to constitute the exterior of the display device 1000. The housing member HM may include a material with relatively high stiffness. For example, the housing member HM may include frames and/or plates each made of glass, plastic, and/or metal.

The housing member HM provides an accommodation space. The display panel DP may be accommodated in the accommodation space and may be protected from external impact.

Hereinafter, referring to FIG. 1B, a schematic cross-sectional view of a pixel disposed in the display area DA according to an embodiment will be described.

Referring to FIG. 1B, a substrate SUB may have various degrees of flexibility. The substrate SUB may be a rigid substrate, or a flexible substrate that can be bent, folded, or rolled.

A buffer layer BF may be disposed on the substrate SUB. The buffer layer BF blocks the transfer of impurities from the substrate SUB to an upper layer of the buffer layer BF, for example, to a semiconductor layer ACT, thereby preventing characteristic degradation of the semiconductor layer ACT and reducing stress. The buffer layer BF may be single-layered or multi-layered including at least one of a silicon oxide (SiOx), a silicon nitride (SiNx), and a silicon oxynitride (SiOxNy). The buffer layer BF may be partially or wholly omitted.

The semiconductor layer ACT is disposed on the buffer layer BF. The semiconductor layer ACT may include at least one of a polysilicon and an oxide semiconductor. The semiconductor layer ACT includes a channel region C, a first region P, and a second region Q. The first region P and the second region Q are respectively disposed on both sides of the channel region C. The channel region C may include a semiconductor doped with a small amount of impurity or undoped with an impurity, and the first region P and the second region Q may include semiconductors doped with a large amount of impurity compared to the channel region C. The semiconductor layer ACT may be formed of an oxide semiconductor. For example, a separate protective layer (not shown) may be added to protect the oxide semiconductor material, which is vulnerable to external environments such as high temperature.

A first insulation layer IL1 is disposed on the semiconductor layer ACT.

A gate electrode GE and a lower electrode CE1 are disposed on the first insulation layer Ill. The lower electrode CE1 may be a part of the gate electrode GE.

A second insulation layer IL2 is disposed on the gate electrode GE and the first insulation layer Ill. The first insulation layer IL1 and the second insulation layer IL2 may be single-layered or multi-layered including at least one of inorganic insulators such as a silicon oxide, a silicon nitride, a silicon oxynitride, an aluminum oxide, a titanium oxide, a tantalum oxide, and a hafnium oxide.

An upper electrode CE2 of a storage capacitor Cst is disposed on the second insulation layer IL2.

The storage capacitor Cst may include a lower electrode CE1 and an upper electrode CE2 that overlap each other, while disposing the second insulation layer IL2 therebetween. According to an embodiment, the gate electrode GE may be the lower electrode CE1 of the storage capacitor Cst, but embodiments are not limited thereto, and the lower electrode CE1 may be formed as an individual electrode.

A third insulation layer IL3 is disposed on the upper electrode CE2. The third insulation layer IL3 may be single-layered or multi-layered including at least one of inorganic insulators such as a silicon oxide, a silicon nitride, a silicon oxynitride, an aluminum oxide, a titanium oxide, a tantalum oxide, and a hafnium oxide.

A source electrode SE and a drain electrode DE are disposed on the third insulation layer IL3. The source electrode SE and the drain electrode DE are respectively electrically connected to a first area P and a second area Q of the semiconductor layer ACT through contact holes formed in the first insulation layer Ill, the second insulation layer IL2, and the third insulation layer IL3.

The source electrode SE and the drain electrode DE may include a conductive material containing molybdenum (Mo), aluminum (Al), copper (Cu), or titanium (Ti), and may be formed as a multi-layered or single layer including the above materials. In an embodiment, the source electrode SE and the drain electrode DE may be formed of a multi-layer structure of a titanium layer, an aluminum layer, and a titanium layer (Ti/Al/Ti).

A fourth insulation layer IL4 is disposed on the third insulation layer IL3, the source electrode SE, and the drain electrode DE. The fourth insulation layer IL4 may include a general-purpose polymer such as polymethyl methacrylate (PMMA) or polystyrene (PS), a polymer derivative having a phenolic group, an acryl-based polymer, an imide-based polymer, an aryl ether-based polymer, an amide-based polymer, a fluorine-based polymer, p-xylene-based polymers, vinyl alcohol-based polymers, and blends thereof.

A connection electrode CE is disposed on the fourth insulation layer IL4. The connection electrode CE may be electrically connected to the drain electrode DE through a contact hole formed in the fourth insulation layer IL4.

The connection electrode CE may include a conductive material containing molybdenum (Mo), aluminum (Al), copper (Cu), or titanium (Ti), and may be formed as a multi-layered or single layer including the above materials. In an embodiment, the connection electrode CE may be formed of a multi-layer structure of a titanium layer, an aluminum layer, and a titanium layer (Ti/Al/Ti).

A fifth insulation layer IL5 is disposed on the connection electrode CE. The fifth insulation layer IL5 may include a general-purpose polymer such as polymethyl methacrylate (PMMA) or polystyrene (PS), a polymer derivative having a phenolic group, an acryl-based polymer, an imide-based polymer, an aryl ether-based polymer, an amide-based polymer, a fluorine-based polymer, p-xylene-based polymers, vinyl alcohol-based polymers, and blends thereof.

A first electrode E1 may be disposed on the fifth insulation layer IL5.

A transistor Tr formed of the gate electrode GE, the semiconductor layer ACT, the source electrode SE, and the drain electrode DE is electrically connected to the first electrode E1 to supply a current to the light emitting element.

A partitioning wall IL6 is disposed on the first electrode E1. The partitioning wall IL6 overlaps at least a part of the first electrode E1. For example, the partitioning wall IL6 may overlap an edge of the first electrode E1. The partitioning wall IL6 includes an opening that defines a light emitting region. For example, a width of the opening exposing an upper surface of the first electrode E1 may correspond to a width of the light emitting region from which light is emitted, or may correspond to a width of the pixel. The opening may have an octagonal shape that is similar to a rhombus or may have a shape like a rhombus in a plan view, but is not limited thereto, and may have any shape such as a quadrangle, a polygon, a circle, or an oval.

A spacer IL7 may be disposed on the partitioning wall IL6. The partitioning wall IL6 and the spacer IL7 may include an organic insulating material such as a general-purpose polymer such as polymethyl methacrylate (PMMA) or polystyrene (PS), a polymer derivative with a phenolic group, an acryl-based polymer, an imide-based polymer, a polyimide, an acryl-based polymer, a siloxane-based polymer, and the like.

An emission layer EML is disposed on the first electrode E1. The emission layer EML may include an organic material and/or an inorganic material. The emission layer EML may generate light having a color. The emission layer EML may be formed to be disposed only within the opening of the partitioning wall IL6 using a mask.

Functional layers ML1 and ML2 may be respectively disposed above and below the emission layer EML. The first functional layer ML1 may include a hole transport region, and the second functional layer ML2 may include an electron transport region.

The functional layers ML1 and ML2 may overlap the entire surface of the display area DA of the substrate SUB. In the display area DA, emission layers EML of different colors according to colors of the corresponding pixels may be disposed to be spaced apart from each other, but the functional layers ML1 and ML2 may be formed to cover the display area DA as a whole. Each of the functional layers ML1 and ML2 may be shared by multiple pixels disposed in the display area DA. Each of the functional layers ML1 and ML2 may cover multiple first electrodes E1.

A second electrode E2 is disposed on the second functional layer ML2.

The first electrode E1, the emission layer EML, and the second electrode E2 may form a light emitting element. In an embodiment, the first electrode E1 may be an anode that is a hole injection electrode, and the second electrode E2 may be a cathode that is an electron injection electrode. However, embodiments are not limited thereto, and depending on a driving method of a light emitting display device, the first electrode E1 may be a cathode and the second electrode E2 may be an anode.

Holes and electrons are respectively injected into the emission layer EML from the first electrode E1 and the second electrode E2, and light emission occurs when excitons that are a combination of the injected holes and electrons transition from an exited state to a ground state.

An encapsulation layer ENC is disposed on the second electrode E2. The encapsulation layer ENC may cover and seal not only the top surface of the light emitting element, but may also seal the side surfaces of the light emitting element. Since the light emitting element is vulnerable to moisture and oxygen, the encapsulation layer ENC seals the light emitting element to block the inflow of external moisture and oxygen.

The encapsulation layer ENC may include multiple layers, among which the encapsulation layer ENC may be formed as a composite film including both an inorganic layer and an organic layer. For example, the encapsulation layer ENC may be formed as a triple layer formed by sequentially stacking a first encapsulation inorganic layer EIL1, an encapsulation organic layer EOL, and a second encapsulation inorganic layer EIL2.

Although not shown in the drawings, a capping layer disposed between the second electrode E2 and the encapsulation layer ENC may be further included. The capping layer may contain an organic material. The capping layer may protect the second electrode E2 from a subsequent sputtering process and may improve light emission efficiency of the light emitting element. The capping layer may have a refractive index equal to or greater than a refractive index of the first encapsulation inorganic layer EIL1.

Figure 2:
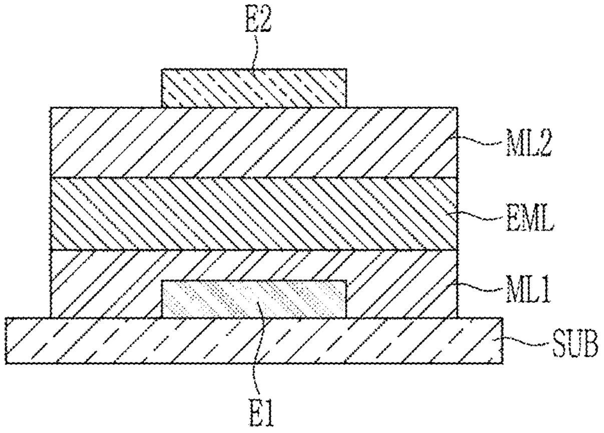
FIG. 2 is a schematic cross-sectional view of the light emitting element according to an embodiment.

Hereinafter, the light emitting element according to an embodiment will be described with reference to FIG. 2. FIG. 2 is a schematic cross-sectional view of a light emitting element according to an embodiment.

As previously described, the light emitting element according to an embodiment includes the first electrode E1 and the second electrode E2 that overlap each other while facing each other. The emission layer EML may be disposed between the first electrode E1 and the second electrode E2.

The light emitting element according to an embodiment further includes the functional layers ML1 and ML2 in addition to the emission layer EML between the first electrode E1 and the second electrode E2. The functional layers ML1 and ML2 may include a hole transport region ML1 and an electron transport region ML2. The light emitting element according to an embodiment may include the first electrode E1, the hole transport region ML1, the emission layer EML, the electron transport region ML2, and the second electrode E2 that are sequentially stacked.

The first electrode E1 has conductivity. The first electrode E1 may be formed of a metal alloy or a conductive compound. The first electrode E1 may be an anode. In an embodiment, the first electrode E1 may be a pixel electrode. The first electrode E1 may be a transmissive electrode, a transflective electrode, or a reflective electrode. When the first electrode E1 is a transmissive electrode, the first electrode E1 may include a transparent metal oxide, for example, indium tin oxide (ITO), indium zinc oxide (IZO), zinc oxide (ZnO), indium tin zinc oxide (ITZO), and the like. When the first electrode E1 is a transflective electrode or a reflective electrode, the first electrode E1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (e.g., a mixture of Ag and Mg). In an embodiment, the first electrode E1 may include layers including a reflective layer or a transflective layer formed of the above-stated material and a transparent conductive layer formed of indium tin oxide (ITO), indium zinc oxide (IZO), zinc oxide (ZnO), indium tin zinc oxide (ITZO), and the like. For example, the first electrode E1 may have a three-layer structure of ITO/Ag/ITO, but is not limited thereto. A thickness of the first electrode E1 may be in a range of about 1,000 Å to about 10,000 Å. For example, the thickness of the first electrode E1 may be in a range of about 1,000 Å to about 3,000 Å.

The hole transport region ML1 is provided on the first electrode E1. The hole transport region ML1 may include at least one of a hole injection layer (HIL), a hole transport layer (HTL), a hole buffer layer, and an electron blocking layer.

The hole transport region ML1 may have a structure of a layer formed of a single material, a layer formed of different materials, or a multi-layer structure having layers formed of different materials.

For example, the hole transport region ML1 may have a single-layer structure of a hole injection layer (HIL) or a hole transport layer (HTL), or may have a single-layer structure including a hole injection material and a hole transport material. In an embodiment, the hole transport region ML1 may have a single-layer structure made of different materials, or a hole injection layer (HIL)/hole transport layer (HTL), a hole injection layer (HIL)/hole transport layer (HTL)/hole buffer layer, a hole injection layer (HIL)/hole buffer layer, a hole transport layer (HTL)/hole buffer layer, or a hole injection layer (HIL)/hole transport layer (HTL)/electron blocking layer, wherein each structure is stacked from the first electrode E1 in its respective stated order, but an embodiment is not limited thereto.

The hole transport region ML1 may be formed by using various methods such as vacuum deposition, spin coating, casting, the LB (Langmuir-Blodgett) technique, inkjet printing, laser printing, and laser thermal imaging (LITI).

The hole injection layer may include, for example, a phthalocyanine compound such as copper phthalocyanine; triphenyl polyether ketones (TPAPEK) including DNTPD (N,N'-diphenyl-N,N'-bis-[4-(phenyl-m-tolyl-amino)-phenyl]-biphenyl-4,4'-diamine), m-MTDATA (4,4',4"-[tris(3-methylphenyl)phenylamino] triphenylamine), TDATA (4,4'4"-tris(N,N-diphenylamino)triphenylamine), 2-TNATA (4,4',4"-tris{N,-(2-naphthyl)-N-phenylamino}-triphenylamine), PEDOT/PSS (poly(3,4-ethylenedioxythiophene)/poly(4-styrenesulfonate)), PANI/DESA (polyaniline/dodecylbenzenesulfonic acid), PANI/CSA (polyaniline/camphor sulfonic acid), PANI/PSS (polyaniline/poly(4-styrenesulfonate)), NPB (N,N'-di(naphthalene-1-yl)-N,N'-diphenyl-benzidine), and amines, 4-isopropyl-4'-methyldiphenyliodonium [tetrakis(pentafluorophenyl)borate], HAT-CN (dipyrazino[2,3-f:2',3'-h] quinoxaline-2,3,6,7,10,11-hexacarbonitrile), and the like.

The hole transport layer may further include, for example, carbazole derivatives such as N-phenylcarbazole and polyvinylcarbazole, fluorine derivatives, TPD (N, N'-bis(3-methylphenyl)-N, N'-diphenyl-[1,1-biphenyl]-4,4'-diamine), triphenylamine derivatives such as TCTA (4,4',4"-tris(N-carbazolyl)triphenylamine), NPB (N,N'-di(naphthalene-1-)yl)-N,N'-diphenyl-benzidine), TAPC (4,4'-[N,N-bis(4-methylphenyl)benzenamine]), HMTPD (4,4'-bis[N,N'-(3-tolyl)amino]-3,3'-dimethylbiphenyl), mCP (1,3-bis(N-carbazolyl)benzene), and the like.

A thickness of the hole transport region ML1 may be in a range of about 50 Å to about 10,000 Å. For example, the thickness of the hole transport region ML1 may be in a range of about 100 Å to about 5,000 Å. A thickness of the hole injection layer (HIL) may be, for example, in a range of about 30 Å to about 1,000 Å, and a thickness of the hole transport layer (HTL) may be in a range of about 30 Å to about 1,000 Å. For example, a thickness of the electron blocking layer may be in a range of about 10 Å to about 1,000 Å. When the thickness of the hole transport region ML1 satisfies the above range, a satisfactory level of hole transport characteristic can be obtained without a substantial increase in driving voltage.

The hole transport region ML1 may further include a charge generating material for conductivity improvement in addition to the above-mentioned materials. The charge generating material may be uniformly or non-uniformly distributed within the hole transport region ML1. The charge generating material may be, for example, a p-dopant. The p-dopant may be one of a quinone derivative, a metal oxide, and a compound containing a cyano group, but is not limited thereto. For example, non-limiting examples of p-dopants include quinone derivatives such as tetracyanoquinodimethane (TCNQ) and F4-TCNQ (2,3,5,6-tetrafluoro-7,7',8,8'-tetracyanoquinodimethane); and metal oxides such as tungsten oxide and molybdenum oxide, but are not limited thereto.

As described above, the hole transport region ML1 may further include at least one of a hole buffer layer and an electron blocking layer in addition to a hole injection layer (HIL) and a hole transport layer (HTL). The hole buffer layer may increase light emission efficiency by compensating for a resonance distance according to a wavelength of light emitted from the emission layer EML. As a material included in the hole buffer layer, a material that can be included in the hole transport region ML1 may be used. The electron blocking layer is a layer that prevents electron injection from the electron transport region ML2 into the hole transport region ML1.

The emission layer EML is provided on the hole transport region ML1. The emission layer EML may have a thickness, for example, in a range of about 100 Å to about 1,000 Å. For example, the emission layer EML may have a thickness in a range of about 100 Å to about 300 Å. The emission layer EML may have a single-layer structure formed of a single material, a single-layer structure formed of different materials, or a multi-layer structure having layers formed of different materials.

The emission layer EML according to an embodiment may include quantum dots. Quantum dots (hereinafter also referred to as semiconductor nanocrystals) may include a group II-VI compound, a group III-V compound, a group IV-VI compound, a group IV compound, a group I-III-VI compound, a group II-III-VI compound, a group I-II-IV-VI compound, or a combination thereof. The quantum dots may not contain cadmium.

The group II-VI compound may be selected from a group consisting of: a binary compound selected from a group consisting of CdSe, CdTe, ZnS, ZnSe, ZnTe, ZnO, HgS, HgSe, HgTe, MgSe, MgS, and a mixture thereof; a tertiary compound selected from a group consisting of AgInS, CuInS, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof; and a quaternary compound selected from a group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof. The II-VI compound may further include a group III metal.

The group III-V compound may be selected from a group consisting of: a binary compound selected from a group consisting of GaN, GaP, GaAs, GaSb, AN, AlP, AlAs, AlSb, InN, InP, InAs, InSb, and a mixture thereof; a tertiary compound selected from a group consisting of GaNP, GaNAs, GaNSb, GaPAs, GaPSb, AlNP, AlNAs, AlNSb, AlPAs, AlPSb, InGaP, InNP, InNAs, InNSb, InPAs, InZnP, InPSb, and a mixture thereof; and a quaternary compound selected from a group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, InZnP, and a mixture thereof. The group III-V compound may include a group II metal (e.g., InZnP).

The group IV-VI compound may be selected from a group consisting of: a binary compound selected from a group consisting of SnS, SnSe, SnTe, PbS, PbSe, PbTe, and a mixture thereof; a tertiary compound selected from a group consisting of SnSeS, SnSeTe, SnSTe, PbSeS, PbSeTe, PbSTe, SnPbS, SnPbSe, SnPbTe, and a mixture thereof; and a quaternary compound selected from a group consisting of SnPbSSe, SnPbSeTe, SnPbSTe, and a mixture thereof.

The group N element or compound may be a single element compound selected from a group consisting of Si, Ge, and a mixture thereof; and a binary compound selected from a group consisting of SiC, SiGe, and a mixture thereof, but embodiments are not limited thereto.

Examples of the group I-III-VI compound may include CuInSe2, CuInS2, CuInGaSe, and CuInGaS, but embodiments are not limited thereto. Examples of the I-II-IV-VI compound may include CuZnSnSe and CuZnSnS, but embodiments are not limited thereto. The group N element or compound may be selected from a group consisting of: a single element selected from a group consisting of Si, Ge, and a mixture thereof; and a binary compound selected from a group consisting of SiC, SiGe, and a mixture thereof.

The group II-III-VI compounds may be selected from a group consisting of ZnGaS, ZnAlS, ZnInS, ZnGaSe, ZnAlSe, ZnlnSe, ZnGaTe, ZnAlTe, ZnlnTe, ZnGaO, ZnAlO, ZnInO, HgGaS, HgAlS, HgInS, HgGaSe, HgAlSe, HgInSe, HgGaTe, HgAlTe, HgInTe, MgGaS, MgAlS, MgInS, MgGaSe, MgAlSe, MgInSe, and a combination thereof, but embodiments are not limited thereto.

The group I-II-IV-VI compounds may be selected from CuZnSnSe and CuZnSnS, but embodiments are not limited thereto.

In an embodiment, the quantum dot may not include cadmium. The quantum dots may include semiconductor nanocrystals based on group III-V compounds including indium and phosphorus. The group III-V compound may further include zinc. The quantum dot may include a semiconductor nanocrystal based on a group II-VI compound including a chalcogen element (e.g., sulfur, cell selenium, tellurium, or combination thereof) and zinc.

In the quantum dot, the above-mentioned binary compound, ternary compound, and/or quaternary compound may exist in a particle at a uniform concentration, or may exist in a particle at partially different concentrations. In an embodiment, a quantum dot may have a core/shell structure wherein a quantum may surround another quantum dot. An interface between the core and the shell may have a concentration gradient in which the concentration of elements in the shell may decrease toward the center.

In embodiments, quantum dots may have a core-shell structure including a core containing the nanocrystals described above and a shell surrounding the core. The shell of the quantum dot may be a protective layer that maintains semiconductor characteristics by preventing chemical modification of the core and/or may be a charging layer that imparts electrophoretic characteristics to the quantum dot. The shell may be single-layered or multi-layered. An interface between the core and the shell may have a concentration gradient in which the concentration of elements in the shell may decrease toward the center. Examples of the shell of the quantum dot may include a metal oxide, a non-metal oxide, a semiconductor compound, or a combination thereof.

For example, the metal oxide or non-metal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and NiO, or a ternary compound such as $MgAl_2O_4$, $CoFe_2O_4$, $NiFe_2O_4$, and $CoMn_2O_4$, but embodiments are not limited thereto.

For example, the semiconductor compound may be CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, and the like, but embodiments are not limited thereto.

An interface between the core and the shell may have a concentration gradient in which the concentration of elements in the shell may decrease toward the center. In an embodiment, the semiconductor nanocrystal may have a structure including a semiconductor nanocrystal core and a multi-layered shell surrounding the semiconductor nanocrystal core. In an embodiment, the multi-layered shell may have two or more layers, for example, two, three, four, five, or more layers. Two adjacent layers of the shell may have a single composition or different compositions. In a multi-layered shell, each layer may have a composition that varies along a radius of the quantum dot.

Quantum dots may have a full width of half maximum (FWHM) of a light emitting wavelength spectrum equal to less than about 45 nm. For example, quantum dots may have a FWHM of a light emitting wavelength spectrum equal to less than about 40 nm. For example, quantum dots may have a FWHM of a light emitting wavelength spectrum equal to less than about 30 nm. Color purity or color reproducibility can be improved in these ranges. Light emitted through the quantum dots may be emitted in all directions, and thus a light viewing angle can be improved.

In the quantum dot, the shell material and the core material may have different energy bandgaps. For example, an energy bandgap of the shell material may be greater than that of the core material. In another embodiment, an energy bandgap of the shell material may be smaller than that of the core material. The quantum dot may have a multi-layered shell. In a multi-layered shell, an energy bandgap of an outer layer may be larger than an energy bandgap of an inner layer (i.e., a layer closer to the core). In a multi-layered shell, an energy bandgap of an outer layer may be smaller than an energy bandgap of an inner layer.

The quantum dots may control an absorption/light emitting wavelength by adjusting the composition and size. A maximum light emitting peak wavelength of a quantum dot may have a wavelength range of ultraviolet (UV) to infrared wavelengths or higher.

In an embodiment, the quantum dots may emit blue light. For example, a maximum light emitting peak wavelength of the quantum dots may be equal to or greater than about 430 nm (e.g., 440 nm or more, 450 nm or more, 451 nm or more, 452 nm or more, 453 nm or more, 454 nm or more, 455 nm or more, 456 nm or more, 457 nm or more, 458 nm or more, 459 nm or more, or 460 nm or more) and equal to or less than about 490 nm (e.g., 480 or less, 470 nm or less, 468 nm or less, 467 nm or less, 466 nm or less, or 465 nm or less).

In an embodiment, the quantum dots may emit green light. A maximum light emitting peak wavelength of the quantum dot may be equal to or greater than about 490 nm (for example, 500 nm or more, 510 nm or more, 520 nm or more, or 530 nm or more) and equal to or less than about 560 nm (for example, 550 nm or less, 545 nm or less, 540 nm or less, or 535 nm or less).

In an embodiment, the quantum dots may emit red light. A maximum light emitting peak wavelength of the quantum dot may be equal to or greater than about 600 nm (for example, 610 nm or more, 615 nm or more, or 620 nm or more) and equal to or less than about 650 nm (for example, 645 nm or less, 640 nm or less, 635 nm or less, or 630 nm or less).

The quantum dot may have a quantum efficiency equal to or greater than about 10%, for example, about 30% or more, about 50% or more, about 60% or more, about 70% or more, about 90% or more, or even 100%. The quantum dot may have a relatively narrow spectrum. The quantum dots may have, for example, a full width at half maximum (FWHM) of a wavelength spectrum equal to less than about 50 nm. For example, the quantum dots may have a FWHM of a light emitting wavelength spectrum equal to less than about 45 nm. For example, the quantum dots may have a FWHM of a light emitting wavelength spectrum equal to less than about 40 nm. For example, the quantum dots may have a FWHM of a light emitting wavelength spectrum equal to less than about 30 nm.

The quantum dot may have a particle size in a range of about 1 nm to about 100 nm. The particle size may be a particle diameter or a diameter converted by assuming a spherical shape from a 2D image obtained by transmission electron microscopy analysis. For example, the quantum dot may have a particle size in a range of about 1 nm to about 20 nm, (for example, 2 nm or more, 3 nm or more, or 4 nm or more and 50 nm or less, 40 nm or less, 30 nm or less, 20 nm or less, 15 nm or less, or 10 nm or less). The shape of the quantum dot is not particularly limited. For example, a shape of the quantum dot may be, but is not limited to, a sphere, a polyhedron, a pyramid, a multi-pod, a square, a rectangular parallelepiped, a nanotube, a nanorod, a nanowire, a nanosheet, or a combination thereof.

Quantum dots may be commercially available or may be synthesized appropriately. The quantum dots may have a relatively freely controlled particle size during colloidal synthesis, and a uniform particle size.

The quantum dot may include an organic ligand (e.g., with hydrophobic and/or hydrophilic moieties). The organic ligand moiety may be bound to a surface of the quantum dot. The organic ligand may include RCOOH, $RNH_2$, $R_2NH$, $R_3N$, RSH, $R_3PO$, $R_3P$, ROH, RCOOR, $RPO(OH)_2$, RHPOOH, $R_2POOH$, or a combination thereof, and each R may independently be a substituted or unsubstituted alkyl of C3 to C40 (e.g., C5 or more and C24 or less), a substituted or unsubstituted aliphatic hydrocarbon group of C3 to C40, or a substituted or unsubstituted aromatic hydrocarbon group of C6 to C40 such as a substituted or unsubstituted alkenyl, or a substituted or unsubstituted aromatic hydrocarbon group of C6 to C40 (e.g., C6 or more and C20 or less) such as a substituted or unsubstituted C6 to C40 aryl group, or a combination thereof.

For example, the organic ligand may be a thiol compound such as methane thiol, ethane thiol, propane thiol, butane thiol, pentane thiol, hexane thiol, octane thiol, dodecane thiol, hexadecane thiol, octadecane thiol, benzyl thiol, and the like; amines such as methane amine, ethane amine, propane amine, butane amine, pentyl amine, hexyl amine, octyl amine, nonyl amine, decyl amine, dodecyl amine, hexadecyl amine, octadecyl amine, dimethyl amine, diethyl amine, dipropyl amine, tributyl amine, trioctyl amine, and the like; a carboxylic acid compound such as methanic acid, ethanoic acid, propionic acid, butanoic acid, pentanoic acid, hexanoic acid, heptanoic acid, octanoic acid, dodecanoic acid, hexadecanoic acid, octadecanoic acid, oleic acid, benzoic acid, and the like; a phosphine compound such as methyl phosphine, ethyl phosphine, propyl phosphine, butyl phosphine, pentyl phosphine, octyl phosphine, dioctyl phosphine, tributyl phosphine, trioctyl phosphine, and the like; a phosphine compound or an oxide compound thereof such as methyl phosphine oxide, ethyl phosphine oxide, propyl phosphine oxide, butyl phosphine oxide, pentyl phosphine oxide, tributyl phosphine oxide, octyl phosphine oxide, dioctyl phosphine oxide, trioctyl phosphine oxide, and the like; diphenyl phosphine, a triphenyl phosphine compound, or an oxide compound thereof; and C5 to C20 alkyl phosphinic acids, such as hexyl phosphinic acid, octyl phosphinic acid, dodecane phosphinic acid, tetradecane phosphinic acid, hexadecane phosphinic acid, and octadecane phosphinic acid; C5 to C20 alkyl phosphonic acids, and the like, but is not limited thereto. The quantum dot may contain a hydrophobic organic ligand alone or as a mixture of one or more. The hydrophobic organic ligand may not contain a photopolymerizable moiety (e.g., an acrylate group, a methacrylate group, and the like).

In an embodiment, the emission layer may include a monolayer of quantum dots. In another embodiment, the emission layer may include a monolayer of quantum dots, or 1 or more, for example, 2 or more, 3 or more, or 4 or more and 20 or less, 10 or less, 9 or less, 8 or less, 7 or less, or 6 or less.

The electron transport region ML2 is provided on the emission layer EML. The electron transport region ML2 may include at least one of a hole blocking layer, an electron transport layer (ETL), and an electron injection layer (EIL), but embodiments are not limited thereto.

The electron transport region ML2 may have a layer formed of a single material, a layer formed of different materials, or a multi-layer structure having layers formed of different materials.

For example, the electron transport region ML2 may have a single-layer structure of an electron injection layer (EIL) or an electron transport layer (ETL), or a single-layer structure formed of an electron injection material and an electron transport material. The electron transport region ML2 may have a single-layer structure formed of different materials, or may have a structure in which an electron transport layer/electron injection layer, a hole blocking layer/electron injection layer/electron transport layer/electron injection layer, wherein each structure is stacked from the emission layer EML in its respective stated order, but embodiments are not limited thereto. A thickness of the electron transport region ML2 may be, for example, in a range of about 1,000 Å to about 1,500 Å.

The electron transport region ML2 may be formed by using various methods such as vacuum deposition, spin coating, casting, the Langmuir-Blodgett (LB) technique, inkjet printing, laser printing, and laser induced thermal imaging (LITI).

When the electron transport region ML2 includes an electron injection layer, the electron transport region may include a metal halide, a lanthanide metal, or a co-deposition material of a metal halide and a lanthanide metal. For example, the metal halide may be an alkali metal halide. For example, the electron transport region ML2 may include LiF, lithium quinolate (Liq), Li2O, BaO, NaCl, CsF, Yb, RbCl, RbI, KI, or KI:Yb, but embodiments are not limited thereto. The electron injection layer (EIL) may also be formed of a mixture of an electron transport material and an insulating organometal salt. For example, the organometal salt may include a metal acetate, a metal benzoate, a metal acetoacetate, a metal acetylacetonate, or a metal stearate. The electron injection layer may have a thickness in a range of about 1 Å to about 100 Å. For example, the electron injection layer may have a thickness in a range of about 3 Å to about 90 Å. When the thickness of the electron injection layer satisfies the ranges as described above, satisfactory electron injection characteristic can be obtained without a substantial increase in driving voltage.

In another embodiment, the electron transport region ML2 may include inorganic oxide nanoparticles. The inorganic oxide may be a metal oxide, for example, zinc oxide, magnesium oxide, zirconium oxide, tin oxide, tungsten oxide, tantalum oxide, hafnium oxide, aluminum oxide, titanium oxide, barium oxide, or any combination thereof. The inorganic oxide nanoparticles may further include elements such as silicon.

In an embodiment, the inorganic oxide nanoparticle may include zinc oxide (ZnO), zinc magnesium oxide (ZnMgO), zinc aluminum oxide (ZnAlO), titanium dioxide ($TiO_2$), magnesium oxide (MgO), zirconium oxide ($ZrO_2$), tin oxide (SnO), tin dioxide ($SnO_2$), tungsten oxide ($WO_3$), tantalum oxide ($Ta_2O_3$), hafnium oxide ($HfO_3$), aluminum oxide ($Al_2O_3$), zirconium silicon oxide ($ZrSiO_4$), barium titanium oxide ($BaTiO_3$), barium zirconium oxide ($BaZrO_3$), or any combination thereof.

In an embodiment, an average diameter of the inorganic oxide nanoparticles may be in a range of about 3 nm to about 15 nm.

The second electrode E2 is provided on the electron transport region ML2. The second electrode E2 may be a common electrode or a cathode. The second electrode E2 may be a transmissive electrode, a transflective electrode, or a reflective electrode. When the second electrode E2 is a transmissive electrode, the second electrode E2 may be formed of a transparent metal oxide, for example, indium tin oxide (ITO), indium zinc oxide (IZO), zinc oxide (ZnO), indium tin zinc oxide (ITZO), and the like.

Figure 3:
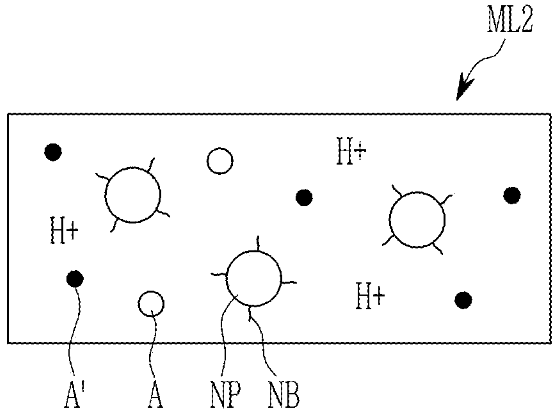
FIG. 3 is a schematic cross-sectional view illustrating an electron transport region.

When the second electrode E2 is a transflective electrode or a reflective electrode, the second electrode E2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (e.g., a mixture of Ag and Mg). In an embodiment, the second electrode E2 may have a multi-layer structure including a reflective layer or transflective layer formed of the above-stated material and a transparent conductive layer formed of indium tin oxide (ITO), indium zinc oxide (IZO), zinc oxide (ZnO), indium tin zinc oxide (ITZO), and the like. Hereinafter, referring to FIG. 3, the electron transport region according to an embodiment will be described in detail. FIG. 3 is a schematic cross-sectional view illustrating an electron transport region.

As shown in FIG. 3, the electron transport region ML2 according to an embodiment may include inorganic oxide nanoparticles NP. The inorganic nanoparticle NP may include zinc oxide (ZnO), zinc magnesium oxide (ZnMgO), zinc aluminum oxide (ZnAlO), titanium dioxide ($TiO_2$), magnesium oxide (MgO), zirconium oxide ($ZrO_2$), tin oxide (SnO), tin dioxide ($SnO_2$), tungsten oxide ($WO_3$), tantalum oxide ($Ta_2O_3$), hafnium oxide ($HfO_3$), aluminum oxide ($Al_2O_3$), zirconium silicon oxide ($ZrSiO_4$), barium titanium oxide ($BaTiO_3$), barium zirconium oxide ($BaZrO_3$), or any combination thereof.

A branch portion NB may be connected to the inorganic nanoparticle NP. The branch portion NB may be a functional group connected to a surface of the inorganic nanoparticle NP, and may include, for example, —OH, —$C_2H_3O_2$, —H, and the like.

The electron transport region ML2 according to an embodiment may include a thermal acid generator (TAG) A. For example, the TAG A may be a material that releases $H^+$ through a process of applying heat, and any kind of TAG A may be used.

The TAG A according to an embodiment may be in a non-ionic form. When a TAG in the form of a salt is provided to a solution for forming the electron transport region, the TAG may react with inorganic nanoparticles before the production of the electron transport region is completed, resulting in deterioration of acid production ability, in particle aggregation, and the like.

The electron transport region ML2 may contain a first material A' in which $H^+$ is separated from the TAG A through a heating process. In a heating process during a manufacturing process, most of the TAG A may be separated into $H^+$ and the first material A', but the TAG A where $H^+$ is not separated and remains in the electron transport region ML2 may also be included.

The TAG according to an embodiment may include a sulfonate-based compound. In an embodiment, the TAG may include a compound represented by Chemical Formula 1 below.

[Chemical Formula 1]

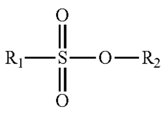

In Chemical Formula 1, $R_1$ and $R_2$ may each independently be a substituted or unsubstituted C3 to C40 alkyl group, a substituted or unsubstituted C3 to C40 aliphatic hydrocarbon group, a substituted or unsubstituted C6 to C40 aromatic hydrocarbon group of C6 to C40, or a combination thereof.

In Chemical Formula 1, the ability to generate $H^+$ may vary depending on $R_1$. For example, when $R_1$ includes a functional group having excellent electron-attracting ability, such as $NO_2$, the $H^+$ generating ability of the TAG may be excellent.

In Chemical Formula 1, $R_2$ may remain in the electron transport region ML2 in a form in which $H^+$ is removed. $R_2$ remaining in the electron transport region ML2 may be a material with a boiling point equal to or greater than about 150° C. and a molecular weight equal to or greater than about 100 g/mol. $R_2$ may include a functional group having a relatively high molecular weight, and thus diffusion to other layers may be prevented.

In other embodiments, $R_2$ may be volatilized through a heating process or an aging process. For example, the boiling point of $R_2$ may be equal to or less than about 150° C., for example 100° C. or less, and thus, $R_2$ may be volatilized through a heating process performed at a temperature in a range of about 100 degrees (° C.) to about 150 degrees (° C.) or through an aging process performed at 100 degrees (° C.) or less.

The TAG A according to an embodiment may include at least one of compounds represented by Chemical Formula 2-1, Chemical Formula 2-2, Chemical Formula 2-3, Chemical Formula 2-4, Chemical Formula 2-5, Chemical Formula 2-6, Chemical Formula 2-7, and Chemical Formula 2-8. In another embodiment, the TAG A may include at least one of compounds represented by Chemical Formula 3-1, Chemical Formula 3-2, Chemical Formula 3-3, Chemical Formula 3-4, Chemical Formula 3-5, and Chemical Formula 3-6.

[Chemical Formula 2-1]

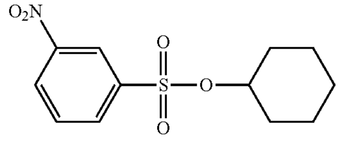

[Chemical Formula 2-2]

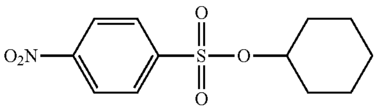

[Chemical Formula 2-3]

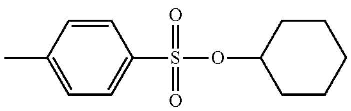

-continued

[Chemical Formula 2-4]

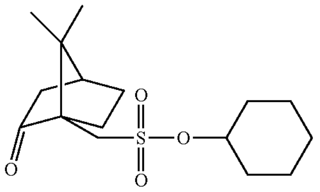

[Chemical Formula 2-5]

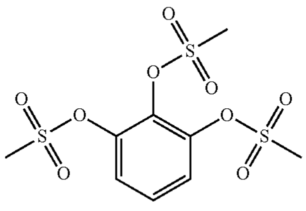

[Chemical Formula 2-6]

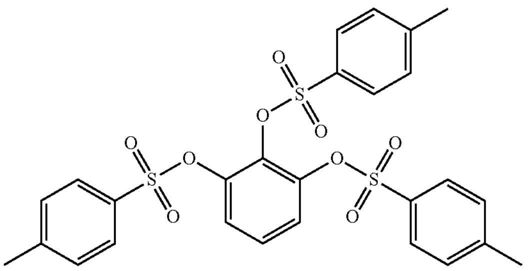

[Chemical Formula 2-7]

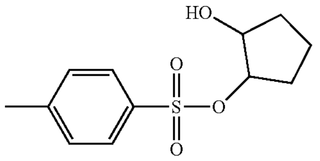

[Chemical Formula 2-8]

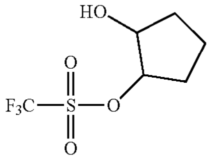

[Chemical Formula 3-1]

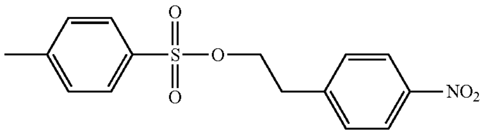

[Chemical Formula 3-2]

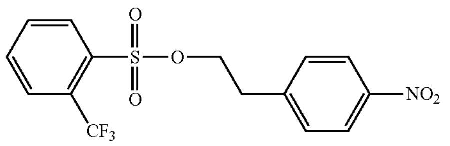

[Chemical Formula 3-3]

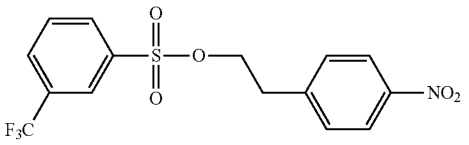

-continued

[Chemical Formula 3-4]

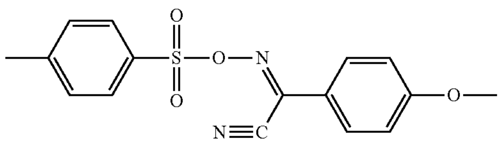

[Chemical Formula 3-5]

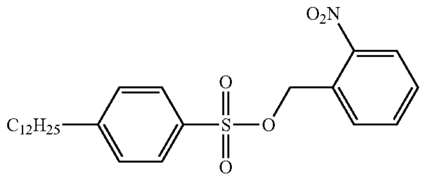

[Chemical Formula 3-6]

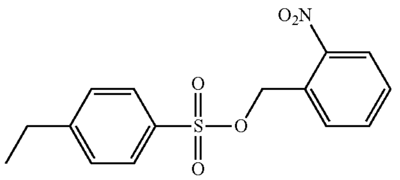

When $R_1$ contains $NO_2$ as in the compound represented by Chemical Formula 2-1 and Chemical Formula 2-2, $NO_2$ may have excellent electron-attracting power. Accordingly, the compounds represented by Chemical Formula 2-1 and Chemical Formula 2-2 may relatively readily generate $H^+$. Even in cases where $R_1$ contains $CF_3$ as in the compounds represented by Chemical Formula 3-2, Chemical Formula 3-3, and Chemical Formula 2-8, $CF_3$ may have excellent electron-attracting power. Accordingly, the compounds represented by Chemical Formula 3-2, Chemical Formula 3-3, and Chemical Formula 2-8 may relatively readily generate $H^+$.

The first material A' (for example, cyclohexene) after $H^+$ is separated from the compound represented by Chemical Formula 2-1 to Chemical Formula 2-8 may have a relatively low boiling point. The first material A' having a relatively low boiling point may be volatilized through a heating process and an aging process.

For example, a compound represented by Chemical Formula 2-1 to Chemical Formula 2-4 may generate cyclohexene, which has a boiling point of about 81 degrees (° C.). For example, a compound represented by Chemical Formula 2-5 to 2-6 may generate benzene, which has a boiling point of about 80 degrees (° C.). For example, a compound represented by Chemical Formula 2-7 may generate cyclopentanol, which has a boiling point of about 140 degrees (° C.). The generated materials described above may be removed through a heating process or an aging process performed at a temperature equal to or less than about 150 degrees (° C.).

In another embodiment, the first material A' after $H^+$ is separated from the compound represented by Chemical Formula 3-1 to Chemical Formula 3-6 may have a relatively high boiling point. Therefore, the first material generated from the compound represented by Chemical Formula 3-1 to Chemical Formula 3-6 may not volatilize through the heating process and the aging process.

A first material A' generated from a compound represented by Chemical Formula 3-1 to Chemical Formula 3-6 may have a relatively high molecular weight. Accordingly, the first material A' may not diffuse into other layers (e.g., an emission layer and the like). Accordingly, unnecessary material movement can be prevented, and reliability of the light emitting element may be maintained.

For example, a compound represented by Chemical Formula 3-1 to Chemical Formula 3-3 may generate a first material having a molecular weight of about 151 g/mol, which may have a boiling point of about 250 degrees (° C.). For example, a compound represented by Chemical Formula 3-4 may generate a first material having a molecular weight of about 160 g/mol. For example, a compound represented by Chemical Formula 3-5 or Chemical Formula 3-6 may generate a first material having a molecular weight of about 137 g/mol, which may have a boiling point of about 222 degrees (° C.).

For example, the TAG A according to an embodiment may include a TAG in the form of an ion, and may include, for example, a compound represented by Chemical Formula 4 below. The ion-type TAG may include a negative ion part and a positive ion part as shown in Chemical Formula 4 below.

[Chemical Formula 4]

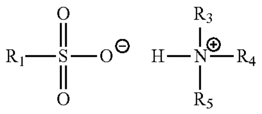

When heat is applied to a compound represented by Chemical Formula 4, the following reaction may occur. The generated by-product may not diffuse into the emission layer, and for example, may be a compound volatilized through a structure having a low boiling point.

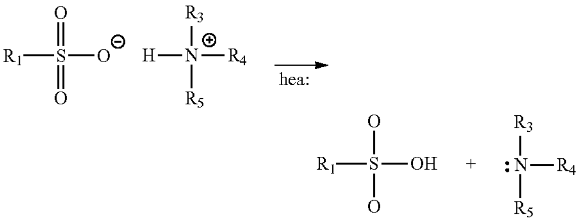

The negative ion part may include a compound represented by one of the following chemical formulas. In the chemical formulas as follows, a hydrogen atom connected to a benzene ring or a cyclohexane ring may be substituted with an alkyl group, $NO_2$, $CF_3$, or the like. In an embodiment, $R_6$ may include a substituted or unsubstituted alkyl group having 1 or more carbon atoms, or a substituted or unsubstituted alkenyl group having 2 or more carbon atoms.

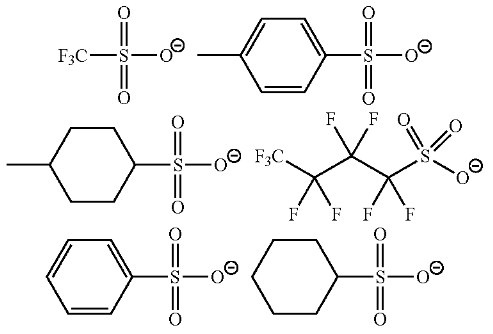

-continued

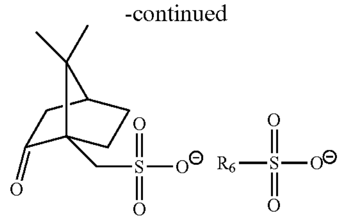

In the compound represented by Chemical Formula 4, the positive ion part may include a pyridine-based compound represented by the chemical formula as follows, or $R_3$, $R_4$, and $R_5$ may each independently be H, $CH_3$, $CH_2$, or $CH_3$. The boiling point of the following pyridine-based compound may be about 115 degrees, and may be removed by volatilization through a heating process or an aging process.

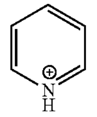

Figure 4:
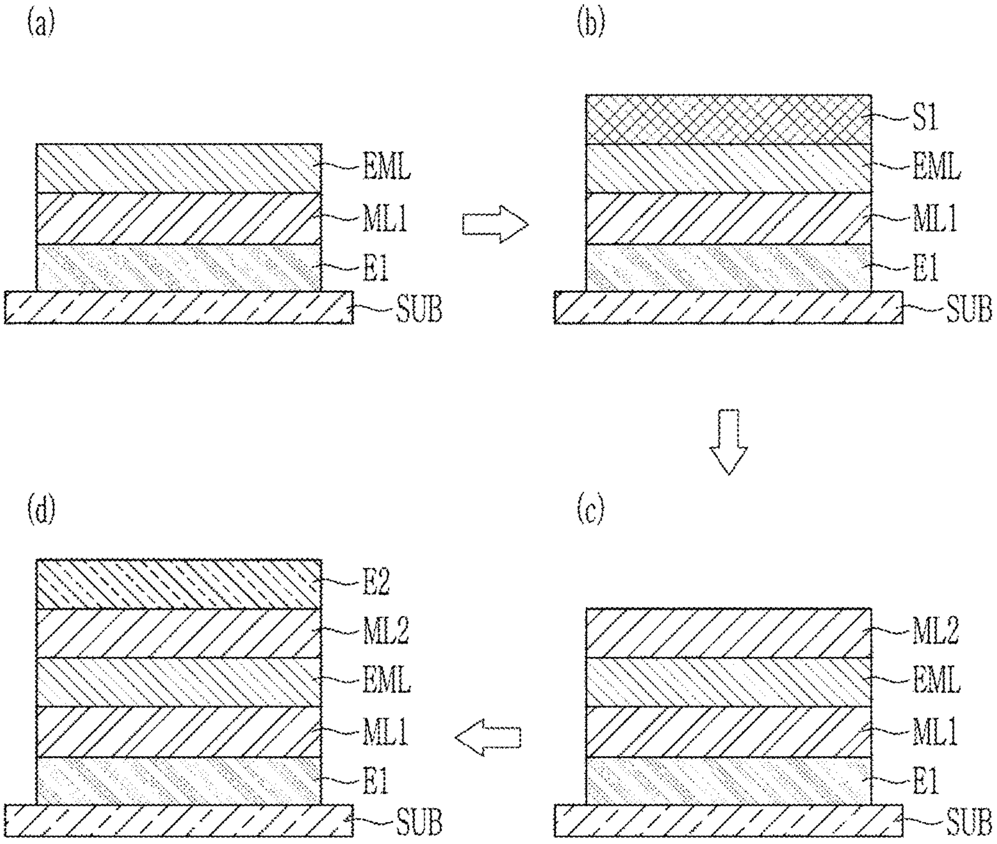
FIG. 4 is a schematic cross-sectional view of a manufacturing process of a light emitting element.
Figure 5:
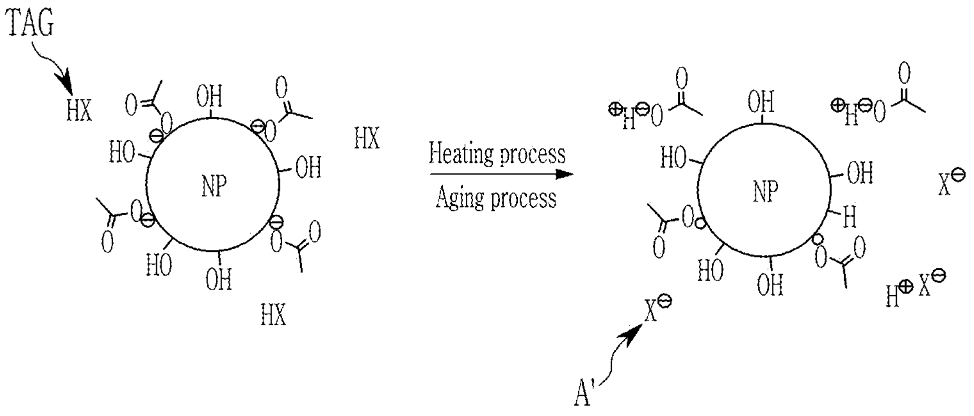
FIG. 5 illustrates a reaction of the electron transport region according to a manufacturing process.

Hereinafter, referring to FIG. 4 and FIG. 5, a manufacturing process of the light emitting element will be described. FIG. 4 is a schematic cross-sectional view of a manufacturing process of the light emitting element, and FIG. 5 shows reaction of the electron transport region according to the manufacturing process.

Referring to FIG. 4, the first electrode E1, the hole transport region ML1, and the emission layer EML are sequentially formed on the substrate SUB, as shown in (a) of FIG. 4.

A first solution 51 is applied on the emission layer EML, and a curing process is performed, as shown in (b) of FIG. 4. The first solution 51 may contain a solvent, inorganic nanoparticles, and the TAG. According to an embodiment, a branch may be connected to the inorganic nanoparticle, and as an example, the branch may include —OH, —$C_2H_3O_2$, and the like. The TAG may be in a dispersed state in the first solution without a separate reaction. The inorganic nanoparticles and the TAG provided in the first solution are shown in (a) of FIG. 5.

The curing process may be carried out at a first temperature. The first temperature may be in a range of about 100 degrees (° C.) to about 150 degrees (° C.). The curing process may be performed, for example, in about 1 to 20 minutes. In the curing process, the TAG contained in the first solution may generate $H^+$.

An aging process may be performed on the cured first solution 51 to form an electron transport region ML2, as shown in (c) of FIG. 4. The aging process may be carried out at about 100 degrees (° C.) or less, for example, it may be carried out at about 50 degrees (° C.) to 80 degrees (° C.). The aging process may be carried out in about an hour to several days. Through the aging process, reaction equilibrium by heat can proceed.

According to the curing process and the aging process, a reaction in which $H^+$ generated from the TAG is connected to inorganic nanoparticles or separates branches connected to inorganic nanoparticles may be performed. Through the aging process, the reaction can reach equilibrium. The state of inorganic nanoparticles and the TAG is shown in (b) of FIG. 5.

$H^+$ generated from the TAG may be connected to inorganic nanoparticles or may perform a reaction to separate the branch, thereby improving the current density of the light emitting element. An n-doping effect may be generated on the light emitting element.

Thereafter, the light emitting element may be manufactured by forming a second electrode E2 on the electron transport region ML2, as shown in (d) of FIG. 4.

According to an embodiment, it is possible to use a TAG to provide $H^+$ at an appropriate point in the manufacturing of the electron transport region. Accordingly, it is possible to prevent overreaction between $H^+$ and inorganic nanoparticles and provide an appropriate reaction, thereby providing a long life-span and highly effective light emitting element.

Figure 6:
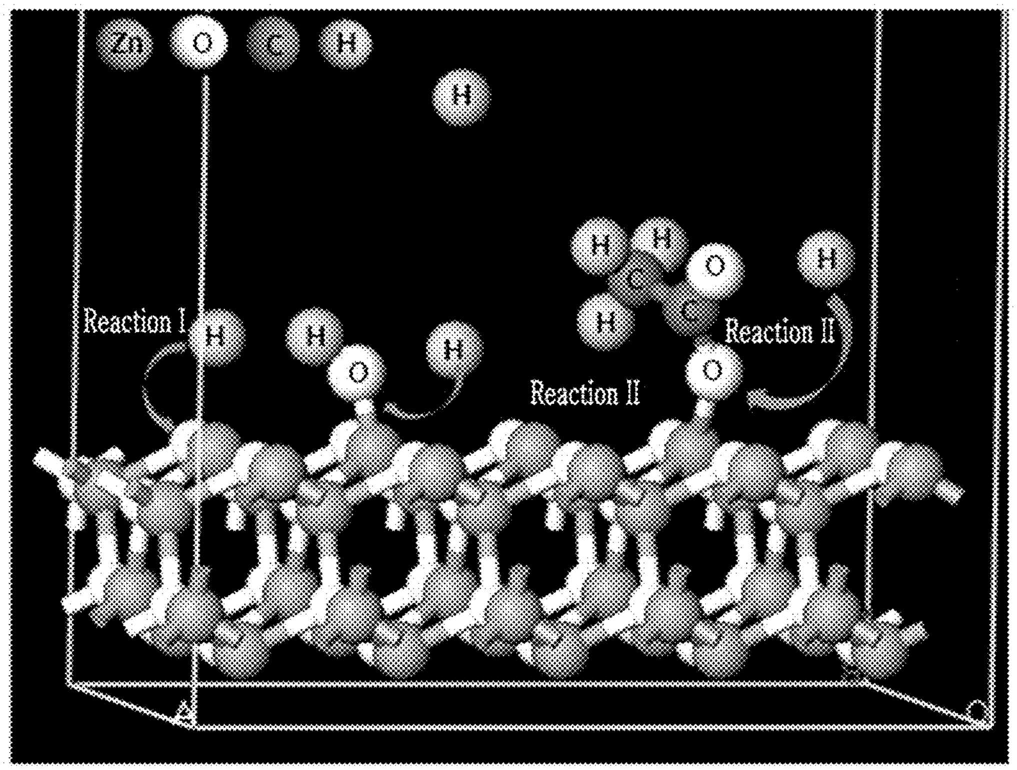
FIG. 6 illustrates a reaction of the electron transport region according to an embodiment.

Hereinafter, referring to FIG. 6, a reaction of the electron transport region according to an embodiment will be schematically described. FIG. 6 shows a reaction of the electron transport region according to an embodiment.

When heat is applied to the TAG through a heating process or an aging process, $H^+$ is generated from the TAG. The generated $H^+$ can be adsorbed to inorganic nanoparticles (e.g., ZnO) included in the electron transport region like reaction I. In another embodiment, the generated $H^+$ may react with the branch part connected to the inorganic nanoparticle (e.g., ZnO) included in the electron transport region as in reaction II, and the branch part may be separated from the inorganic nanoparticle. For example, the inorganic nanoparticles may have a form in which —OH or —$C_2H_3O_2$ is connected thereto, and the —OH or —$C_2H_3O_2$ may react with $H^+$ to be separated from the inorganic nanoparticles.

Figure 7A:
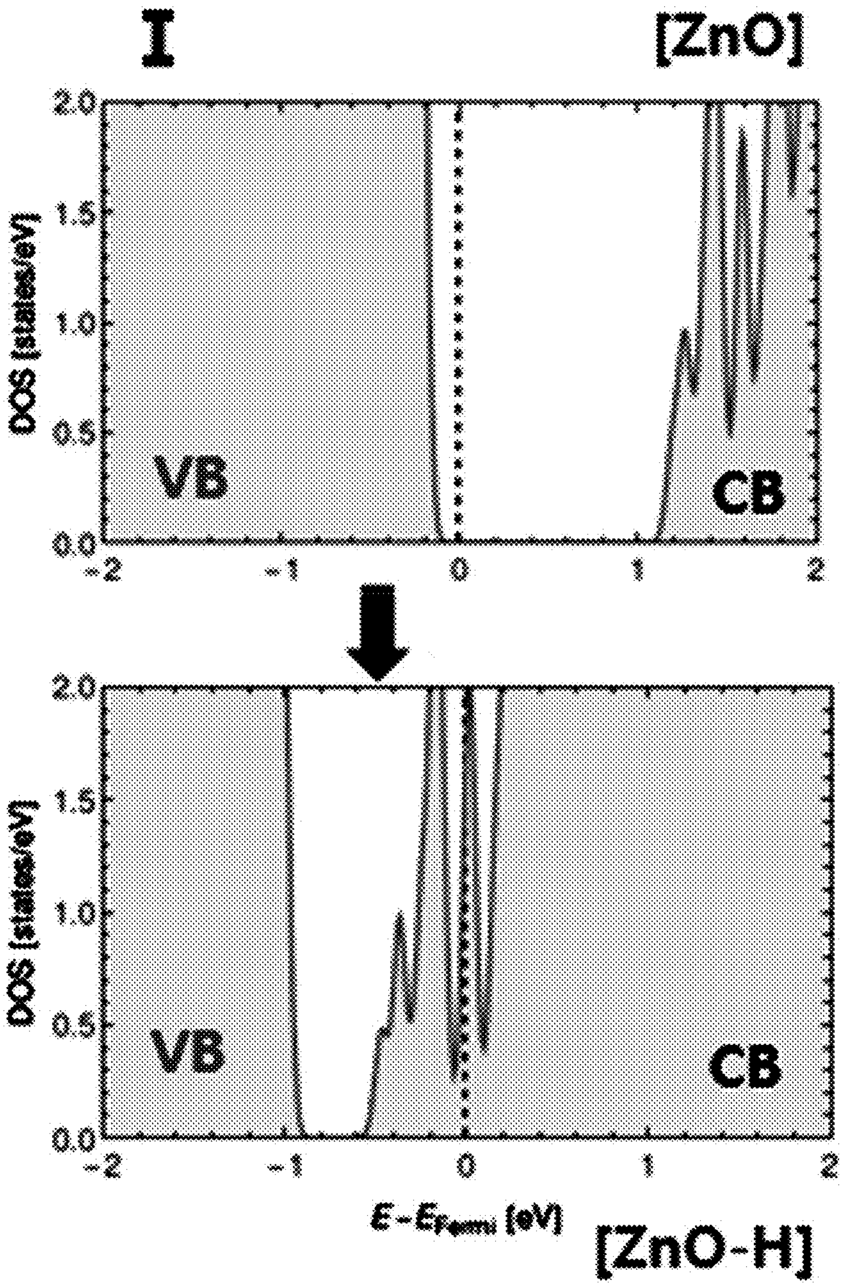
FIG. 7A is a graph that illustrates a density of state (DOS) according to Reaction I.

Hereinafter, an effect according to reaction I and reaction II of FIG. 6 will be described with reference to FIG. 7A and FIG. 7B. FIG. 7A is a graph that shows a density of state (DOS) according to reaction I, and FIG. 7B is a graph that shows a DOS according to reaction II.

Referring to FIG. 7A, it was determined that when $H^+$ is adsorbed to inorganic nanoparticles (ZnO) according to an embodiment, the Fermi level (represented by a dotted line) moved to a region that overlaps with a conduction band CB between a balance band VB and a conduction band CB. Thus, it was determined that the n-doping effect appeared as $H^+$ was adsorbed to the inorganic nanoparticles.

Figure 7B:
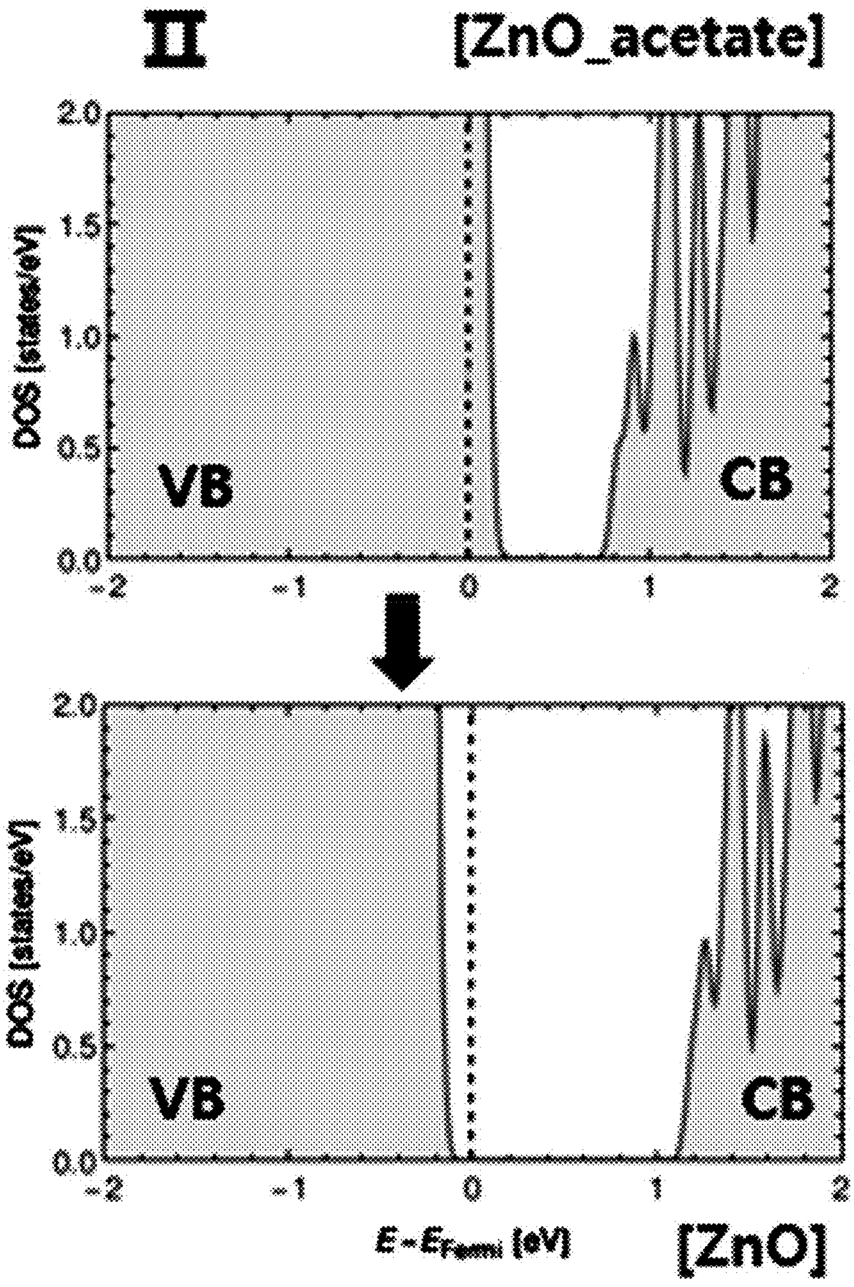
FIG. 7B is a graph that illustrates a DOS according to Reaction II.

Referring to FIG. 7B, it was determined that when the branch part connected to the inorganic nanoparticle reacts with $H^+$ and thus is separated from the branch part according to an embodiment, the Fermi level moved between the balance band VB and the conduction band CB at a position where the dotted line representing the Fermi level overlaps the balance band VB. Thus, it was determined that the n-doping effect appeared as the branch part adsorbed to the inorganic nanoparticle.

According to an embodiment, it can be determined that the TAG provides $H^+$ to the electron transport region, for example, to inorganic nanoparticles during the manufacturing process, resulting in the n-doping effect.

Figure 8:
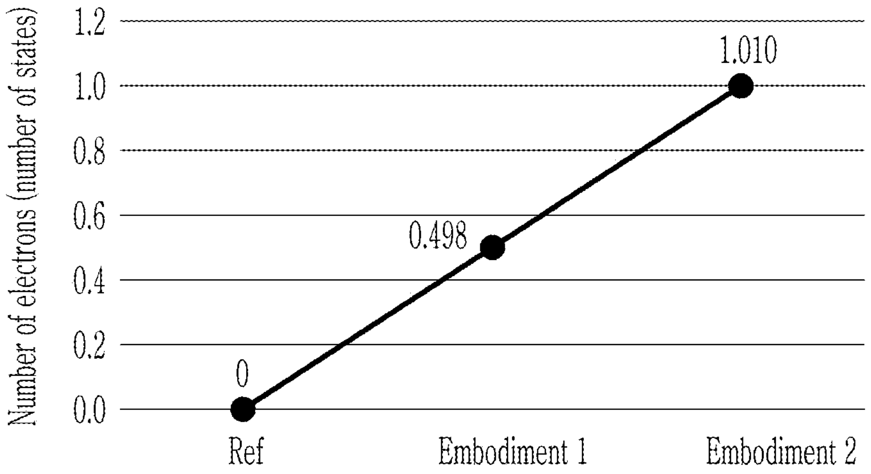
FIG. 8 is a graph illustrating the number of donating electrons according to the number of $H^+$ adsorbed to the inorganic nanoparticle included in the electron transport region.

FIG. 8 is a graph illustrating the number of donating electron according to the number of $H^+$ adsorbed to the inorganic nanoparticle included in the electron transport region.

In FIG. 8, Ref denotes a case that the number of $H^+$ adsorbed to the inorganic nanoparticle is 0, Embodiment 1 denotes a case that the number of $H^+$ adsorbed to the inorganic nanoparticle is 1, and Embodiment 2 denotes a case that the number of $H^+$ adsorbed to the inorganic nanoparticle is 2.

Referring to FIG. 8, It was determined that the number of donating electrons increased as the number of $H^+$ adsorbed to the inorganic nanoparticles increased. Thus, it was determined that ability to provide electrons was improved, and it was determined that the increase in current density was improved by providing $H^+$ by the TAG. According to this, it can be determined that as the number of $H^+$ provided to the inorganic nanoparticles increases, even when the branch part is separated by a large amount, the ability to provide electrons is improved and the increase in current density is improved.

Figure 9:
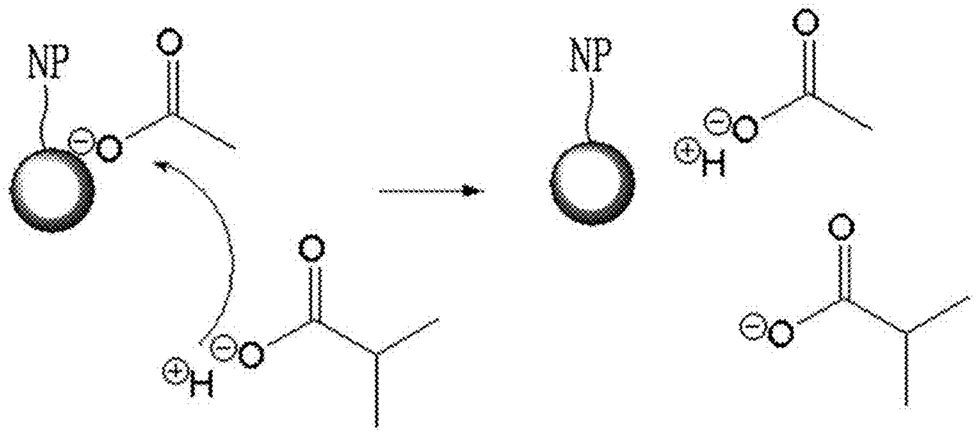
FIG. 9 is a schematic illustration of a reaction of an electron transport region according to a comparative example.

FIG. 9 is a schematic illustration of a reaction of an electron transport region according to a comparative example.

Referring to FIG. 9, when an acid that simply provides $H^+$ rather than TAG is directly provided to inorganic nanoparticle NP, the inorganic nanoparticles NP and $H^+$ can react within a short time in the electron transport region according to a comparative example. A branch part connected to the inorganic nanoparticles (e.g., acetate) may be separated in excess in an initial stage of the process. Thus, a dispersion system in the existing solvent (for example, ethanol) may collapse, resulting in aggregation of the inorganic nanoparticles.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the claims.

What is claimed is:

1. A light emitting element comprising:

a first electrode;

a second electrode overlapping the first electrode;

an emission layer disposed between the first electrode and the second electrode; and an electron transport region disposed between the emission layer and the second electrode, wherein the electron transport region comprises a thermal acid generator (TAG) and inorganic nanoparticles, wherein the TAG generates $H^+$ upon thermal treatment, and wherein the $H^+$ is adsorbed on the inorganic nanoparticles, and wherein the inorganic nanoparticles comprise zinc oxide (ZnO).

2. The light emitting element of claim 1, wherein the electron transport region comprises a material in which $H^+$ is separated from the TAG.

3. The light emitting element of claim 1, wherein the TAG comprises a sulfonate-based compound.

4. The light emitting element of claim 3, wherein the TAG comprises a compound represented by Chemical Formula 1:

[Chemical Formula 1]

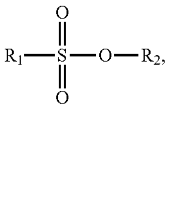

wherein in Chemical Formula 1, $R_1$ and $R_2$ are each independently a substituted or unsubstituted C3 to C40 alkyl group, a substituted or unsubstituted C3 to C40 aliphatic hydrocarbon group, a substituted or unsubstituted C6 to C40 aromatic hydrocarbon group of C6 to C40, or a combination thereof.

5. The light emitting element of claim 4, wherein the compound represented by Chemical Formula 1 comprises at least one compound each independently represented by one of Chemical Formula 2-1, Chemical Formula 2-2, Chemical Formula 2-3, Chemical Formula 2-4, Chemical Formula 2-5, Chemical Formula 2-6, Chemical Formula 2-7, Chemical Formula 2-8, Chemical Formula 3-1, Chemical Formula 3-2, Chemical Formula 3-3, Chemical Formula 3-4, Chemical Formula 3-5, and Chemical Formula 3-6:

[Chemical Formula 2-1]

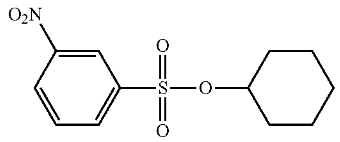

[Chemical Formula 2-2]

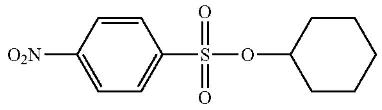

[Chemical Formula 2-3]

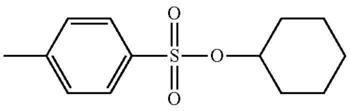

[Chemical Formula 2-4]

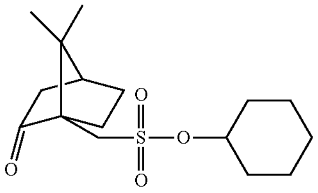

[Chemical Formula 2-5]

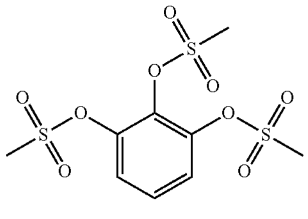

[Chemical Formula 2-6]

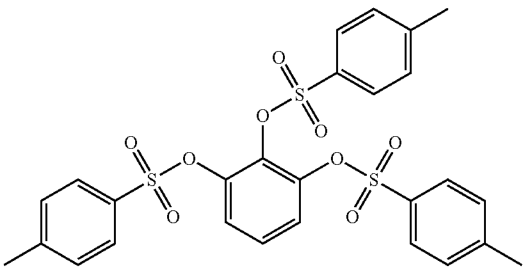

-continued

[Chemical Formula 2-7]

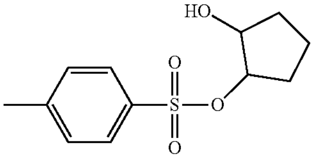

[Chemical Formula 2-8]

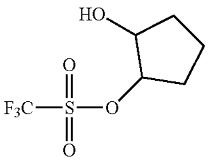

[Chemical Formula 3-1]

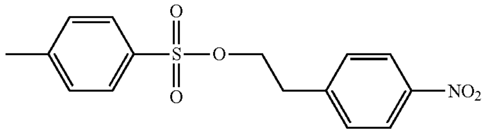

[Chemical Formula 3-2]

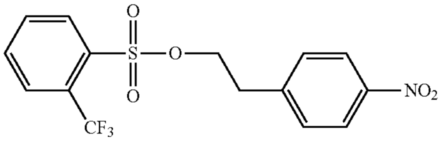

[Chemical Formula 3-3]

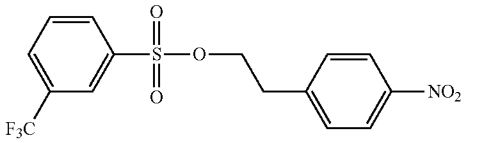

[Chemical Formula 3-4]

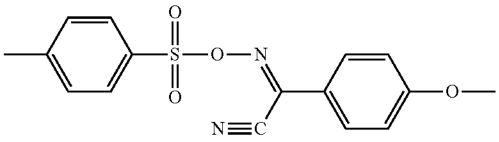

[Chemical Formula 3-5]

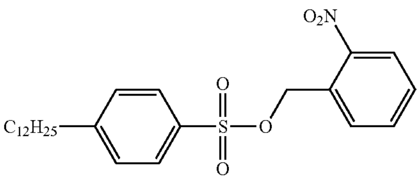

[Chemical Formula 3-6]

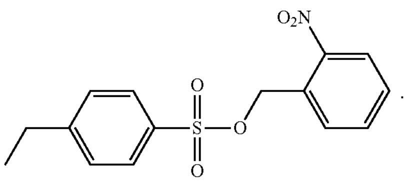

6. The light emitting element of claim 1, wherein the emission layer comprises quantum dots.

7. The light emitting element of claim 1, wherein
the first electrode is an anode,
the second electrode is a cathode, and
the electron transport region comprises at least one of a hole blocking layer, an electron transport layer, and an electron injection layer.

8. A method of manufacturing a light emitting element, comprising:
forming a first electrode;
forming an emission layer on the first electrode;
forming an electron transport region on the emission layer; and
forming a second electrode on the electron transport region, wherein
the forming of the electron transport region comprises:
applying a solution including inorganic nanoparticles and a thermal acid generator (TAG); and
curing the solution,
wherein the TAG generates $H^+$ upon thermal treatment, and wherein the $H^+$ is adsorbed on the inorganic nanoparticles,
wherein in the curing of the solution, the TAG generates $H^+$,
wherein the H+ generated in the curing separates a branch part adsorbed on the inorganic nanoparticle.

9. The method of manufacturing the light emitting element of claim 8, wherein the TAG comprises a sulfonate-based compound.

10. The method of manufacturing the light emitting element of claim 9, wherein the TAG comprises a compound represented by Chemical Formula 1:

[Chemical Formula 1]

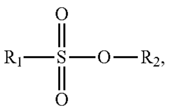

wherein in Chemical Formula 1,
$R_1$ and $R_2$ are each independently a substituted or unsubstituted C3 to C40 alkyl group, a substituted or unsubstituted C3 to C40 aliphatic hydrocarbon group, a substituted or unsubstituted C6 to C40 aromatic hydrocarbon group of C6 to C40, or a combination thereof.

11. The method of manufacturing the light emitting element of claim 9, wherein the compound represented by Chemical Formula 1 comprises at least one compound each independently represented by one of Chemical Formula 2-1 to Chemical Formula 2-8:

[Chemical Formula 2-1]

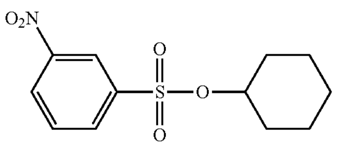

[Chemical Formula 2-2]

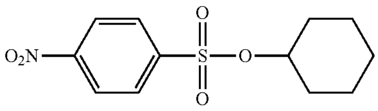

[Chemical Formula 2-3]

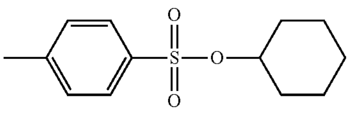

-continued

[Chemical Formula 2-4]

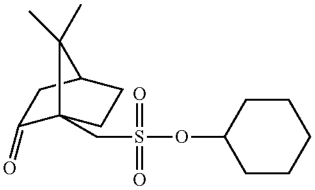

[Chemical Formula 2-5]

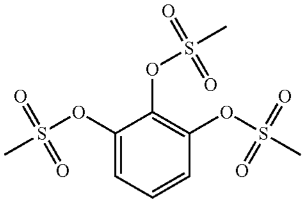

[Chemical Formula 2-6]

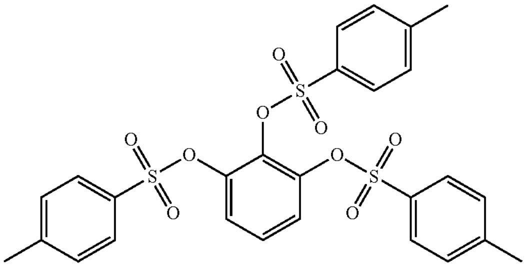

[Chemical Formula 2-7]

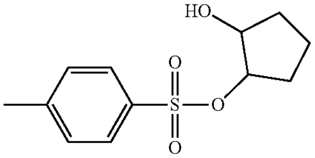

[Chemical Formula 2-8]

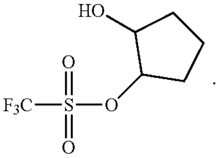

12. The method of manufacturing the light emitting element of claim 9, wherein the compound represented by Chemical Formula 1 comprises at least one compound each independently represented by one of Chemical Formula 3-1 to Chemical Formula 3-6:

[Chemical Formula 3-1]

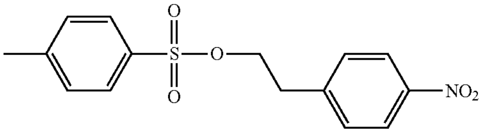

-continued

[Chemical Formula 3-2]

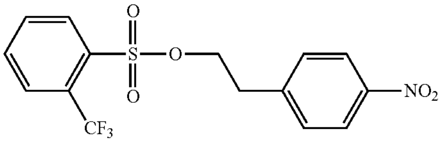

[Chemical Formula 3-3]

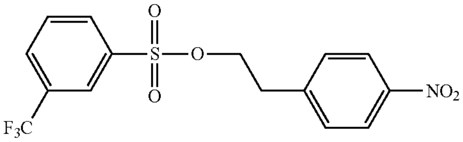

[Chemical Formula 3-4]

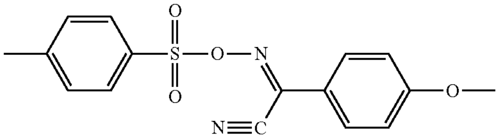

[Chemical Formula 3-5]

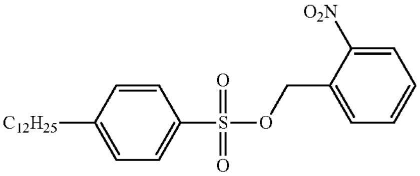

[Chemical Formula 3-6]

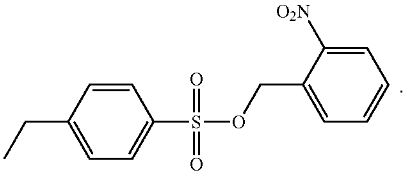

13. The method of manufacturing the light emitting element of claim 9, wherein the emission layer comprises quantum dots.

14. The method of manufacturing the light emitting element of claim 9, wherein the curing is carried out at a first temperature in a range of about 100 degrees (° C.) to about 150 degrees (° C.).

15. The method of manufacturing the light emitting element of claim 14, further comprising aging after the curing of the solution.

16. The method of manufacturing the light emitting element of claim 15, wherein the aging is carried at a second temperature that is lower than the first temperature.

* * * * *